US012649758B2

(12) United States Patent
Lian et al.

(10) Patent No.: US 12,649,758 B2
(45) Date of Patent: Jun. 9, 2026

(54) **INDUSTRIAL METHOD FOR SIMULTANEOUSLY PREPARING *STEVIA REBAUDIANA* CHLOROGENIC ACID AND STEVIOSIDE**

(71) Applicant: Chenguang Biotech Group Co., Ltd., Hebei (CN)

(72) Inventors: Yunhe Lian, Hebei (CN); Meili Xu, Hebei (CN); Wei Gao, Hebei (CN); Zhiping Niu, Hebei (CN); Yanfang Wang, Hebei (CN)

(73) Assignee: Chenguang Biotech Group Co., Ltd., Hebei (CN)

( * ) Notice: Subject to any disclaimer, the term of this patent is extended or adjusted under 35 U.S.C. 154(b) by 99 days.

(21) Appl. No.: 17/215,910

(22) Filed: Mar. 29, 2021

(65) Prior Publication Data

US 2021/0230200 A1 Jul. 29, 2021

Related U.S. Application Data

(63) Continuation of application No. PCT/CN2019/108615, filed on Sep. 27, 2019.

(30) Foreign Application Priority Data

Sep. 30, 2018 (CN) ........................ 201811159815.9

(51) Int. Cl.

| | |
|---|---|
| ***C07H 15/256*** | (2006.01) |
| ***B01D 11/04*** | (2006.01) |
| ***C07C 67/56*** | (2006.01) |
| ***C07C 69/732*** | (2006.01) |
| ***C07H 1/08*** | (2006.01) |

(52) U.S. Cl.

CPC ............... *C07H 1/08* (2013.01); *B01D 11/04* (2013.01); *B01D 11/0492* (2013.01); *C07C 67/56* (2013.01); *C07H 15/256* (2013.01); *C07C 69/732* (2013.01); *C07C 2601/14* (2017.05); *C07C 2601/16* (2017.05)

(58) Field of Classification Search

CPC .......... B01J 3/006; B01D 1/00; B01D 1/0011; B01D 11/04; B01D 11/0492; C07H 15/256; C07H 1/08; C07C 69/732

See application file for complete search history.

(56) References Cited

U.S. PATENT DOCUMENTS

| | | | | |
|---|---|---|---|---|
| 7,862,845 | B2 * | 1/2011 | Magomet | A23G 3/36 426/489 |
| 2017/0000175 | A1 | 1/2017 | Gandhi et al. | |
| 2018/0168212 | A1 * | 6/2018 | Markosyan | A23G 1/48 |

FOREIGN PATENT DOCUMENTS

| | | | | |
|---|---|---|---|---|
| CN | 101062077 | | 10/2007 | |
| CN | 102512473 | * | 6/2012 | A23L 1/30 |
| CN | 103641718 | * | 3/2014 | C07C 67/48 |
| CN | 102617667 | | 7/2014 | |
| CN | 102617667 B | * | 7/2014 | |
| CN | 104710312 | | 6/2015 | |
| CN | 106236808 | | 12/2016 | |
| CN | 105001281 | | 2/2018 | |
| CN | 109438241 | | 3/2019 | |
| MX | 2017010491 A1 | * | 3/2019 | A01N 25/00 |

OTHER PUBLICATIONS

English machine translation of CN105001281, downloaded form worldwide.espacenet.com (Year: 2015).*

English machine translation of CN102617667, downloaded form worldwide.espacenet.com (Year: 2012).*

"Chlorogenic Acid (CAS 327-97-9)", downloaded from https://www.scbt.com/p/chlorogenic-acid-327-97-9 (Year: 2023).*

English machine translation of CN103641718, downloaded form worldwide.espacenet.com (Year: 2014).*

English machine translation of CN102512473, downloaded from worldwide.espacenet.com (Year: 2012).*

English Machine Translation of CN102617667B, downloaded from worldwide.espacenet.com (Year: 2014).*

Iwai et al., "In vitro antioxidative effects and tyrosinase inhibitory activities of seven hydroxycinnamoyl derivatives in green coffee beans," J. Agric. Food Chem., 52 (15), 4893, 2004.

Ooi et al., "Antiviral activities of purified compounds from *Youngia japonica* (L.) DC (Asteraceae, Compositae)", J. Ethnopharmacol, 106 (2), 187, 2006.

(Continued)

*Primary Examiner* — Andrea Olson

(57) ABSTRACT

Disclosed is an industrial method for simultaneously preparing *Stevia rebaudiana* chlorogenic acid and stevioside. The industrial method includes carrying out alcohol extraction on *Stevia rebaudiana* which is used as a raw material, and then adjusting the feed liquid state to allow chlorogenic acid to be in a free molecular state; carrying out extraction separation by a water-insoluble moderate-polarity organic solvent; enriching the *Stevia rebaudiana* chlorogenic acid in an organic layer; and enriching the stevioside in a water layer. Compared with a traditional water extraction process, the method has the advantages that chlorogenic acid ingredient in the *Stevia rebaudiana* can be prevented from being hydrolyzed, such that the contents and effects of effective ingredients in *Stevia rebaudiana* chlorogenic acid products can be guaranteed; effective separation can be carried out on the premise that the quality and the production efficiency of stevioside products are unaffected, the production efficiency can be improved, and the ratio of isochlorogenic acid to total chlorogenic acid in the resulting products is close to that in the raw material; production water consumption can be reduced, and discharge of sewage and flocculation residues can be decreased; and accordingly, the method is a green production process with high benefits.

13 Claims, 3 Drawing Sheets

(56) References Cited

OTHER PUBLICATIONS

Peluso et al., “Studies on the Inhibitory Effects of Caffeoylquinic Acids on Monocyte Migration and Superoxide Ion Production”, J. Nat. Prod., 58, 5, 639-646, 1995.

Zhang et al, “3,5-Dicaffeoylquinic acid isolated from Artemisia argyi and its ester derivatives exert anti-Leucyl-tRNA synthetase of Giardia lamblia (GlLeuRS) and potential anti-giardial effects”, Fitoterapia, 83, 1281-1285, 2012.

Fiamegos, et al., “Antimicrobial and efflux pump inhibitory activity of caffeoylquinic acids from Artemisia absinthium against gram-positive pathogenic bacteria”, PLoS One, 6 (4), 18127, 2011.

Harrison, Jr. et al., “Contents of Caffeoylquinic Acid Compounds in the Storage Roots of Sixteen Sweetpotato Genotypes and Their Potential Biological Activity”, JASHS, 133 (4), 492, 2008.

Chen, “Study of plant cell wall deconstruction during dilute acid-base pretreatment” Beijing Forestry University, 2016.

“Determination of chlorogenic acid and its antioxidant activity in Mian Yin Chen extract” published in Jiangsu Chinese Medicine, vol. 41, No. 4, p. 57, 2009.

Rongfu et al., “Method for the Detection of Stevioside in Food and Beverages” Institute of Polymer Chemistry of Nankai University, p. 19-23, 2020.

Sun, “Extraction and purification techniques of red pigment of Ziziphiopogon japonica” published in China Food Additives, College of Life Science Linyi University, 2011, pp. 99-102.

* cited by examiner

INDUSTRIAL METHOD FOR SIMULTANEOUSLY PREPARING *STEVIA REBAUDIANA* CHLOROGENIC ACID AND STEVIOSIDE

CROSS-REFERENCE TO RELATED APPLICATIONS

The present application is a continuation of International Patent Application Number PCT/CN2019/108615 filed Sep. 27, 2019, which claims priority to Chinese Patent Application Number CN 201811159815.9 filed Sep. 30, 2018, the content of which is incorporated herein by reference in its entirety.

TECHNICAL FIELD

The present invention belongs to the technical field of plant extracts, and relates to an industrial method for simultaneously and efficiently preparing *Stevia rebaudiana* chlorogenic acid and stevioside.

BACKGROUND ART

*Stevia rebaudiana* belongs to a perennial herb of the Compositae family. *Stevia rebaudiana* is native to Paraguay and Brazil in south America, is currently known as one of the sugar plants with relatively high sweetness, and has become the third natural sugar source after sucrose and beet sugar. At present, China is the world's largest producer and supplier of stevioside, accounting for 80% and more of the global total yield. In addition to stevioside, *Stevia rebaudiana* also contains a relatively high content of phenols, and these phenols have important biological activities. *Stevia rebaudiana* has been used as sweet tea and medicinal tea for more than one hundred years in its provenance.

Stevioside is a sweet component in *Stevia rebaudiana*, and is a kaurene diterpene glycoside. Stevioside contains multiple glycosyl fragments in its molecule, is easily soluble in water, and is a zero-calorie high-power sweetener (its calorie is 300 to 500 times of sucrose). The index components specified in GB 8270-2014 mainly include: 9 components such as stevioside, rebaudioside A, rebaudioside B, rebaudioside C, rebaudioside D, rebaudioside F, dulcoside A, rubusoside, steviolbioside and the like.

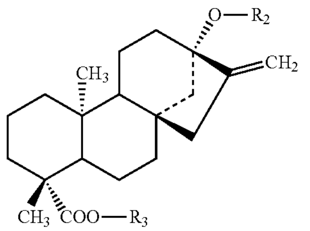

| Name of Compound | | | |
|---|---|---|---|
| Chinese Name | English Name | $R_1$ substituent | $R_2$ substituent |
| 甜菊苷 | stevioside | β-Glc | β-Glc-β-Glc(2→1) |
| 瑞鲍迪苷A | rebaudioside A | β-Glc | β-Glc-β-Glc(2→1)<br>β-Glc(3→1) |
| 瑞鲍迪苷B | rebaudioside B | H | β-Glc-β-Glc(2→1)<br>β-Glc(3→1) |

-continued

| Name of Compound | | | |
|---|---|---|---|
| Chinese Name | English Name | $R_1$ substituent | $R_2$ substituent |
| 瑞鲍迪苷C | rebaudioside C | β-Glc | B-Glc-α-Rha(2→1)<br>β-Glc(3→1) |
| 瑞鲍迪苷D | rebaudioside D | β-Glc-β-Glc(2→1) | β-Glc-β-Glc(2→1)<br>β-Glc(3→1) |
| 瑞鲍迪苷F | rebaudioside F | β-Glc | β-Glc-β-Xyl(2→1)<br>β-Glc(3→1) |

| Name of Compound | | | |
|---|---|---|---|
| Chinese Name | English Name | $R_1$ substituent | $R_2$ substituent |
| 杜克苷A | dulcoside A | β-Glc | B-Glc-α-Rha(2→1) |
| 甜茶苷 | rubusoside | β-Glc | β-Glc |
| 甜菊双糖苷 | steviolbioside | H | β-Glc-β-Glc(2→1) |

The main phenolic substances in *Stevia rebaudiana* are chlorogenic acids (with a content of 4% to 6% in the raw material, HPLC), wherein the isochlorogenic acid substituted by dicaffeoyl accounts for 80% of the total acids. Studies have shown that isochlorogenic acid has many important biological effects, such as anti-oxidation (J. Agric. Food Chem., 2004, 52 (15), 4893), anti-inflammation (J. Nat. Prod., 1995, 58 (5), 639), anti-bacterial and anti-viral (JASHS, 2008, 133 (4), 492; Fitoterapia, 2012, 83, 1281; PLOS One, 2011, 6 (4), 18127; J. Ethnopharmacol, 2006, 106 (2), 187) and the like.

Traditional *Stevia rebaudiana* industry uses water extraction, but isochlorogenic acid is prone to hydrolysis during the extraction process. As shown in FIGS. 1 to 3, the proportion of isochlorogenic acid (dicaffeoylquinic acid) in the water extract solution is greatly reduced, the proportions of mono-caffeoylquinic acid and caffeic acid are increased significantly, and the proportion of isochlorogenic acid in the product obtained by this patented technology is close to that of the raw material.

The separation of phenolic substances from stevioside in *Stevia rebaudiana* is mostly achieved by resin separation. For example, US200710111313.4 and patent No. 201610745221 both use the polarity difference between phenolic substances and glycosides in *Stevia rebaudiana* to achieve the separation of the two types of components through a resin separation step. With this method, there is competitive adsorption between phenolic substances and glycosides in *Stevia rebaudiana*. During the adsorption process, *Stevia rebaudiana* chlorogenic acid occupies part of the adsorption sites of stevioside, such that the resin adsorption capacity of stevioside is reduced, resulting in reduced production efficiency and increased production costs. However, the technology of the present patent application realizes the separation of *Stevia rebaudiana* chlorogenic acid from *Stevia rebaudiana* stevioside before resin adsorption, thereby avoiding such problems.

Compared with mono-caffeoyl chlorogenic acid, isochlorogenic acid has less polarity and enhanced fat solubility (mono-caffeoyl chlorogenic acid is easily soluble in water, its solubility in water is 4% at 25° C., and it is very slightly soluble in ethyl acetate and hardly soluble in a lipophilic organic solvent). The technology of the present patent application uses the dissolution property of *Stevia rebaudiana* chlorogenic acid to separate it from stevioside through extraction. Patent No. CN 102617667 B uses organic solvent extraction to separate the chlorogenic acid component in *Stevia rebaudiana*. However, chlorogenic acid still has a certain solubility in water, if direct extraction is carried out, the effect is not ideal, and only part of the chlorogenic acid products can be obtained. For example, in comparative patent No. CN 102617667 B, in the product spectrum of patent No. CN 102617667 B as shown in FIG. 1, the peak corresponding to 17.808 min is the main component (accounting for about 40%), but this component is not found in the product spectrum (FIG. 2 and FIG. 3). As mentioned above, *Stevia rebaudiana* chlorogenic acid has important biological effects, but there is still no relevant product launched on the market so far for the following main reasons:

(1) In the traditional water extraction process, the isochlorogenic acid in *Stevia rebaudiana* is hydrolyzed, and the process is affected by various factors such as enzymes and temperature. The process is not easy to control, the content of *Stevia rebaudiana* isochlorogenic acid is reduced, and the stability of product quality is poor.

(2) The stevioside is difficult to separate from *Stevia rebaudiana* chlorogenic acid due to their close polarities.

SUMMARY OF THE INVENTION

Due to the above-mentioned defects, the present invention provides an industrial method for simultaneously and efficiently preparing *Stevia rebaudiana* chlorogenic acid and stevioside, which overcomes the above technical difficulties, realizes the industrial production of *Stevia rebaudiana* chlorogenic acid and stevioside at the same time on the premise of ensuring the quality of stevioside and the functional components of *Stevia rebaudiana* chlorogenic acid not being damaged, and lays a foundation for promoting the comprehensive utilization of *Stevia rebaudiana* resources. In addition, compared with the traditional water extraction process, this process also effectively reduces water consumption during production, reduces the discharge of sewage and flocculation residues, and is a green production process with high benefits that can greatly promote the progress of the industry.

In studies, the inventor has found that the traditional *Stevia rebaudiana* industry uses water extraction, but isochlorogenic acid is prone to hydrolysis during the extraction process, and thus the proportion of chlorogenic acid in the water extract solution is greatly reduced, and the proportions of mono-caffeoylquinic acid and caffeic acid are increased significantly. Furthermore, this process is affected by various factors such as enzymes and temperature, and the process is not easy to control, as a result, the content of *Stevia rebaudiana* chlorogenic acid is reduced, and the stability of product quality is poor.

In order to improve the comprehensive utilization value of *Stevia rebaudiana* and accelerate its comprehensive utilization process, the present invention provides an industrial method for simultaneously preparing *Stevia rebaudiana* chlorogenic acid and stevioside.

The present invention adopts the following technical solutions to achieve the above-mentioned purpose of the present invention:

An industrial method for simultaneously preparing *Stevia rebaudiana* chlorogenic acid and stevioside, comprising: carrying out alcohol extraction on *Stevia rebaudiana* which is used as a raw material, and then adjusting the feed liquid state to allow chlorogenic acid to be in a free molecular state; carrying out extraction separation with a water-insoluble organic solvent of moderate-polarity to obtain an organic layer enriched with chlorogenic acid and a water layer enriched with stevioside.

During the adjustment of the feed liquid state to allow chlorogenic acid to be in a free molecular state, the feed liquid is adjusted using a reagent with pKa <4.7 to allow chlorogenic acid to be in a free molecular state.

Preferably, the reagent with pKa <4.7 is selected from one or more of $NaH_2PO_4$, $H_3PO_4$, HCl, $NaHSO_4$, $H_2SO_4$, $H_2CO_3$, $HNO_3$, citric acid, formic acid, oxalic acid, succinic acid, and benzoic acid.

The alcohol extraction is carried out by extraction with an aqueous solution of a short-chain alcohol containing 1 to 3 carbon atoms. Preferably, the short-chain concentration of the aqueous solution is at least 70% by volume. More preferably, the extraction is carried out at 40° C. to 60° C.

Preferably, the polarity of the water-insoluble organic solvent of moderate-polarity is 2.0 to 4.5. More preferably, such organic solvent is one or more selected from ethyl acetate, dichloromethane, chloroform, diethyl ether, and propyl ether. Further preferably, by volume, the amount of the organic solvent is 0.8 to 1.5 times of the solution to be extracted.

In the method of the present invention, before extraction, the short-chain alcohol is used to leach *Stevia rebaudiana*, at a material-liquid ratio of 1:(3 to 7). Preferably, the step of alcohol extraction is repeated for 1 to 3 times.

Further, after the alcohol extraction and before adjustment of the feed liquid state, the alcohol extract solution is concentrated at a temperature of 50° C. to 60° C. under a vacuum degree of −0.08 MPa. Preferably, the alcohol extract solution is concentrated 5 to 10 times.

In the *Stevia rebaudiana* chlorogenic acid-enriched extract obtained by extraction with the above method, the proportion of the active ingredient is close to that in the *Stevia rebaudiana* raw material, and it can be seen that there is almost no waste of the active substance. With the industrial method of the present invention, in the obtained *Stevia rebaudiana* chlorogenic acid-enriched extract, the purity of total *Stevia rebaudiana* isochlorogenic acid is >60%.

The water layer obtained by the extraction separation is subjected to resin adsorption separation to obtain stevioside. The resin is a low-polarity divinylbenzene type adsorption resin, and the resin includes T28, ADS-750, 69M, DM30, 201-H and the like. Preferably, by weight, the amount of the resin is 0.5 to 1 time of the obtained water layer.

Preferably, before the resin adsorption, the solid content of the water layer obtained by separation is adjusted to 8% to 12%. By adjusting the solid content, water can be saved and sewage can be reduced.

In the method for preparing stevioside of the present invention, the resin adsorption separation comprises: subjecting the water layer to adsorption with stevioside resin, desalination, decolorization, and separation and purification through refine resin.

Preferably, the flow rate during the adsorption is 0.1 to 0.4 BV/h.

After the adsorption is completed, the resultant is subjected to washing with water, and desorption, the desorbed solution is subjected to desalination, decolorization, and refine separation of stevioside, and drying to obtain the stevioside product.

Preferably, a short-chain alcohol solution is selected for the desorption, wherein the short-chain alcohol concentration of the short-chain alcohol solution for desorption is lower than the short-chain alcohol concentration of the short-chain alcohol solution for extraction. Further, the short-chain alcohol concentration of the short-chain alcohol solution for desorption is controlled to be 70% to 75% by volume; the amount used for the desorption is 1 to 2 BV, and the flow rate during desorption is 1 to 2 BV/h.

Preferably, the method for simultaneously preparing *Stevia rebaudiana* chlorogenic acid and stevioside according to the present invention comprises the following steps:

(1) extracting *Stevia rebaudiana* powder with a short-chain alcohol to obtain an extract solution;

(2) concentrating the extract solution to recover the short-chain alcohol solution and obtain a concentrated solution;

(3) adjusting the feed liquid state to allow chlorogenic acid to be in a free molecular state;

(4) subjecting the solution obtained in (3) to extraction separation, and collecting the organic layer to obtain a *Stevia rebaudiana* chlorogenic acid extract; and (5) subjecting the water layer obtained in (4) to resin adsorption to obtain a stevioside extract.

The present invention overcomes many technical difficulties (including current situations where *Stevia rebaudiana* chlorogenic acid is prone to hydrolysis during the extraction process, and stevioside cannot be separated from *Stevia rebaudiana* chlorogenic acid), provides an industrial method for efficiently preparing *Stevia rebaudiana* chlorogenic acid and stevioside, realizes the industrial production of *Stevia rebaudiana* chlorogenic acid and stevioside at the same time on the premise of ensuring the quality of stevioside and the functional components of *Stevia rebaudiana* chlorogenic acid not being damaged, and lays a foundation for promoting the comprehensive utilization of *Stevia rebaudiana* resources. In addition, compared with the traditional water extraction process, this process also effectively reduces the water consumption during production, reduces the discharge of sewage and flocculation residues, and is a green production process with high benefits that can greatly promote the progress of the industry.

The present invention also provides a *Stevia rebaudiana* chlorogenic acid extract and a stevioside extract prepared according to any one of the above technical solutions.

Preferably, the purity (content) of isochlorogenic acid in the *Stevia rebaudiana* chlorogenic acid extract is >60%.

The beneficial effects produced by using the above technical solutions are as follows:

(1) Compared with the traditional water extraction process, the extraction technology disclosed in the present application can prevent the hydrolysis of the *Stevia rebaudiana* isochlorogenic acid component, so as to ensure the content and efficacy of the active ingredient of the *Stevia rebaudiana* chlorogenic acid product.

(2) This process realizes the effective separation of *Stevia rebaudiana* chlorogenic acid without affecting the quality and production efficiency of the stevioside product, and the production efficiency is greatly improved. The ratio of isochlorogenic acid to total chlorogenic acid in the obtained product is close to that in the raw material.

(3) Compared with the traditional water extraction process, this process greatly reduces the water consumption during production, reduces the discharge of sewage and flocculation residues, and is a green production process with high efficiency that can greatly promote the progress of the industry.

DETAILED DESCRIPTION OF THE INVENTION

Figure 1:
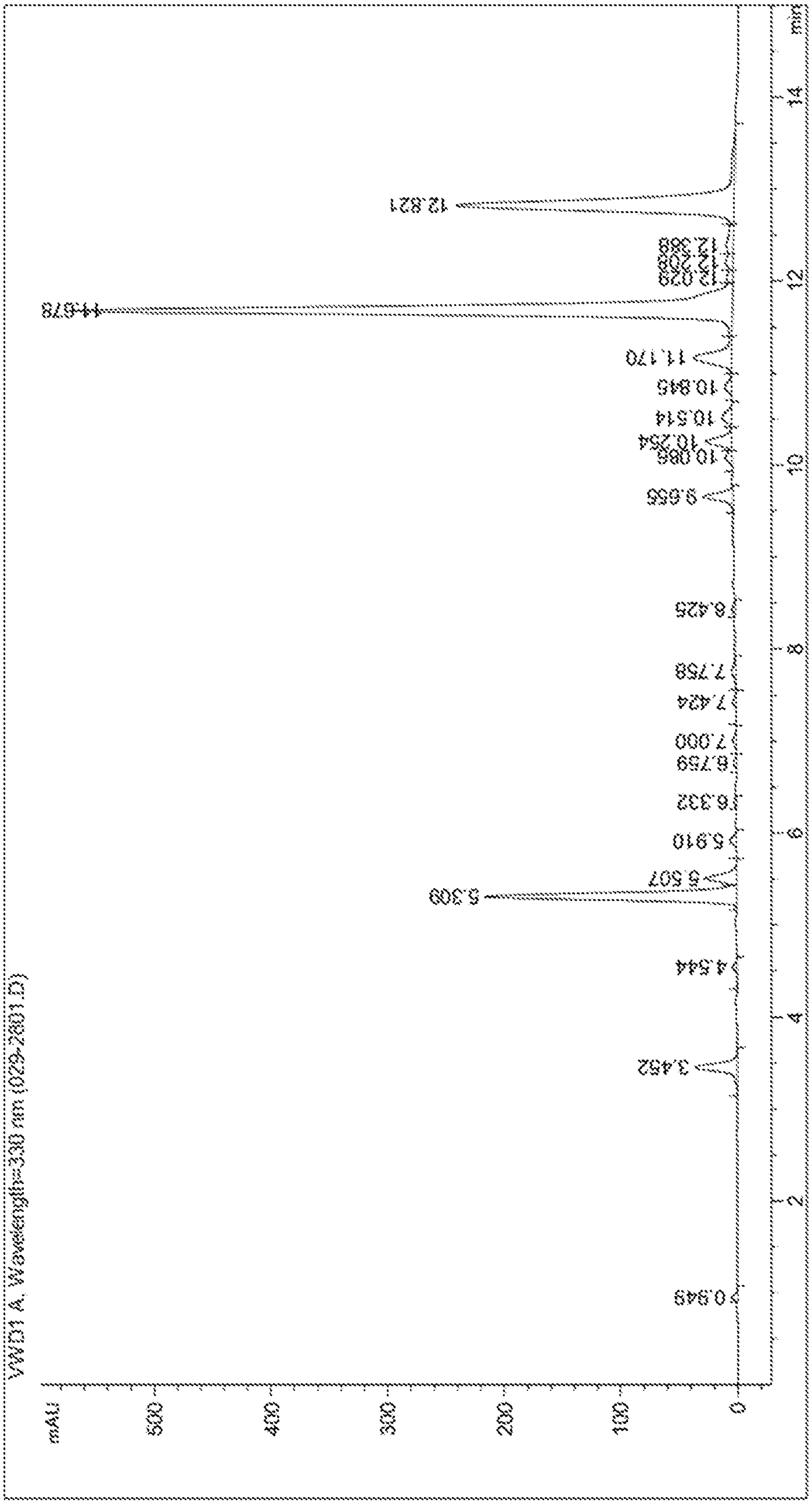
FIG. 1 shows the spectrum of chlorogenic acid in the *Stevia rebaudiana* raw material.

The following Examples are intended to illustrate the present invention, but are not intended to limit the scope of the present invention.

Example 1

The present invention provides an industrial method for preparing *Stevia rebaudiana* chlorogenic acid and the product obtained thereby. The specific steps of the method were as follows:

(1) 1 kg of *Stevia rebaudiana* powder was weighed, and subjected to extraction for three times (at a material-liquid ratio of 1:5/3.5/3.5, respectively) at 50° C. with 85% aqueous ethanol as an extracting liquid. The first extraction was performed for 1.5 h, the second extraction and third extraction were performed for 1 h, and the filtrates were combined as an extract solution.

(2) The extract solution was concentrated 10 times in water bath at 60° C. and a vacuum of −0.08 MPa to recover ethanol.

(3) Online monitoring was performed using a potentiometric titrator, the feed liquid state was adjusted with an aqueous solution of $H_3PO_4$ under continuous stirring, and the addition of the aqueous solution of $H_3PO_4$ was stopped when the electrode potential suddenly jumped.

(4) the feed liquid obtained in the previous process step was extracted with an equal volume of chloroform for 3 times, and the organic phase was concentrated, and subjected to resin purification to obtain 78.5 g of a *Stevia rebaudiana* chlorogenic acid product, with a content of total *Stevia rebaudiana* chlorogenic acid of 82%, and a content of isochlorogenic acid of 65%.

Example 2

The present invention provides an industrial method for preparing *Stevia rebaudiana* chlorogenic acid and the product obtained thereby. The specific steps of the method were as follows:

(1) 1 kg of *Stevia rebaudiana* powder was weighed, and was subjected to extraction twice (at a material-liquid ratio of 1:6/4.5, respectively) at 50° C. with 95% aqueous methanol as an extracting liquid. The first extraction was performed for 1.5 h, the second extraction was performed for 1 h, and the filtrates were combined as an extract solution.

(2) The extract solution was concentrated 10 times in water bath at 60° C. and a vacuum of −0.08 MPa to recover methanol.

(3) Online monitoring was performed using a PHS-3C PH meter, the feed liquid state was adjusted with an aqueous solution of $H_2SO_4$ under continuous stirring, and the addition of the aqueous solution of $H_2SO_4$ was stopped when the electrode potential was 180 mV.

(4) the feed liquid obtained in the previous process step was extracted with an equal volume of ethyl acetate for 3 times, and the organic phase was concentrated, and subjected to resin purification to obtain 75.2 g of a *Stevia rebaudiana* isochlorogenic acid product, with a content of total *Stevia rebaudiana* chlorogenic acid of 84%, and a content of isochlorogenic acid of 66%.

Example 3

The present invention provides an industrial method for preparing *Stevia rebaudiana* chlorogenic acid and the product obtained thereby. The specific steps the method were as follows:

(1) 1 kg of *Stevia rebaudiana* powder was weighed, and was subjected to extraction twice (at a material-liquid ratio of 1:6/4.5, respectively) at 50° C. with 75% aqueous propanol as an extracting liquid. The first extraction was performed for 1.5 h, the second extraction was performed for 1 h, and the filtrates were combined as an extract solution.

(2) The extract solution was concentrated 10 times in water bath at 60° C. and a vacuum of −0.08 MPa to recover propanol.

(3) Online monitoring was performed using a PHS-3C PH meter, the feed liquid state was adjusted with an aqueous solution of formic acid under continuous stirring, and the addition of the aqueous solution of formic acid was stopped when the pH was 3.0.

(4) the feed liquid obtained in the previous process step was extracted with an equal volume of diethyl ether for 3 times, and the organic phase was concentrated, and then subjected to resin purification to obtain 72.8 g of a *Stevia rebaudiana* chlorogenic acid product, with a content of total *Stevia rebaudiana* chlorogenic acid of 90%, and a content of isochlorogenic acid of 73%.

Example 4

The present invention provides an industrial method for preparing *Stevia rebaudiana* chlorogenic acid and the product obtained thereby. The specific steps of the method were as follows:

(1) 1 kg of *Stevia rebaudiana* powder was weighed, and was subjected to extraction for three times (at a material-liquid ratio of 1:5/3.5/3.5, respectively) at 50° C. with 70% aqueous ethanol as an extracting liquid. The first extraction was performed for 1.5 h, each of the second extraction and the third extraction was performed for 1 h, and the filtrates were combined as an extract solution.

(2) The extract solution was concentrated 10 times in water bath at 60° C. and a vacuum of −0.08 MPa to recover ethanol.

(3) Online monitoring was performed using a potentiometric titrator, the feed liquid state was adjusted with an aqueous solution of $HNO_3$ under continuous stirring, and the addition of the aqueous solution of $HNO_3$ was stopped when the electrode potential suddenly jumped.

(4) the feed liquid obtained in the previous process step was extracted with an equal volume of dichloromethane for 3 times, and the organic phase was concentrated, and subjected to resin purification to obtain 79.8 g of a *Stevia rebaudiana* chlorogenic acid product, with a content of total *Stevia rebaudiana* chlorogenic acid of 82%, and a content of isochlorogenic acid of 64%.

Example 5

The present invention provides an industrial method for preparing *Stevia rebaudiana* chlorogenic acid and the product obtained thereby. The specific steps of the method were as follows:

(1) 1 kg of *Stevia rebaudiana* powder was weighed, and was subjected to extraction for three times (at a material-liquid ratio of 1:5/4/3.5, respectively) at 50° C. with 80% aqueous methanol as an extracting liquid. The first extraction was performed for 1.5 h, the second and third extractions were performed for 1 h, and the filtrates were combined as an extract solution.

(2) The extract solution was concentrated 10 times in water bath at 60° C. and a vacuum of −0.08 MPa to recover methanol.

(3) Online monitoring was performed using a potentiometric titrator, the feed liquid state was adjusted with an aqueous solution of HCl under continuous stirring, and the addition of the aqueous solution of HCl was stopped when the electrode potential suddenly jumped.

(4) the feed liquid obtained in the previous process step was extracted with an equal volume of propyl ether for 3 times, and the organic phase was concentrated, and subjected to resin purification to obtain 76.3 g of a *Stevia rebaudiana* chlorogenic acid product, with a content of total *Stevia rebaudiana* chlorogenic acid of 85% and a content of isochlorogenic acid of 65%.

Example 6

The present Example provides an industrial method for preparing stevioside and the product obtained thereby. The specific steps of the method were as follows:

After the feed liquid obtained in step (4) of Example 1 was extracted for 3 times, the solid content of the water layer obtained was adjusted to 10%, and then adsorption was performed using T28 resin in an amount of 1.5 L, at an adsorption flow rate of 0.2 BV/h. After the adsorption was completed, washing was performed using 2 BV of water, wherein the flow rate of the 1st BV of water was 0.2 BV/h, and the flow rate of the 2nd BV of water was BV/h. After water-washing, desorption was performed with 2 BV of 70% aqueous ethanol at a desorption flow rate of 1 BV/h. The desorbed solution was concentrated, desalted, decolorized, refined and dried to obtain 99 g stevioside product. The product was a white powder with a total stevia glycoside (TSG) of 94.3%, and a light transmittance of 90.8% at 420 nm, and the stevioside product has a specific absorbance of 0.012 at 370 nm under a concentration of 1%.

Example 7

The present Example provides an industrial method for preparing stevioside and the product obtained thereby. The specific steps of the method were as follows:

After the feed liquid obtained in step (4) of Example 2 was extracted for 3 times, the solid content of the water layer obtained was adjusted to 8%, and then adsorption was performed using 201-H resin in an amount of 1.5 L, at an adsorption flow rate of 0.25 BV/h. After the adsorption was completed, washing was performed using 2 BV of water, wherein the flow rate of the 1st BV of water was 0.25 BV/h, and the flow rate of the 2nd BV of water was 1 BV/h. After water-washing, desorption was performed with 2 BV of 70% aqueous ethanol at a desorption flow rate of 1 BV/h. The desorbed solution was concentrated, desalted, decolorized, refined and dried to obtain 100.5 g of a stevioside product. The product was a white powder with a TSG of 92.9%, and a light transmittance of 90.3% at 420 nm, and the stevioside product has a specific absorbance of 0.015 at 370 nm under a concentration of 1%.

Example 8

The present Example provides an industrial method for preparing stevioside and the product obtained thereby. The specific steps of the method were as follows:

After the feed liquid obtained in step (4) of Example 3 was extracted for 3 times, the solid content of the water layer obtained was adjusted to 6%, and then adsorption was performed using DM30 resin in an amount of 1.5 L, at an adsorption flow rate of 0.3 BV/h. After the adsorption was completed, washing was performed using 2 BV of water, wherein the flow rate of the 1st BV of water was 0.3 BV/h, and the flow rate of the 2nd BV of water was 1 BV/h. After water-washing, desorption was performed with 2 BV of 70% aqueous ethanol at a flow rate of 1 BV/h. The desorbed solution was concentrated, desalted, decolorized, refined and dried to obtain 99.7 g of a stevioside product. The product was a white powder with a TSG of 93.6%, and a light transmittance of 90.6% at 420 nm, and the stevioside product has a specific absorbance of 0.010 at 370 nm under a concentration of 1%.

Comparative Example 1

The present Comparative Example provides a method for preparing stevioside and chlorogenic acid, which was operated according to the method provided by Chinese Patent Publication No. CN106236808B.

Figure 2:
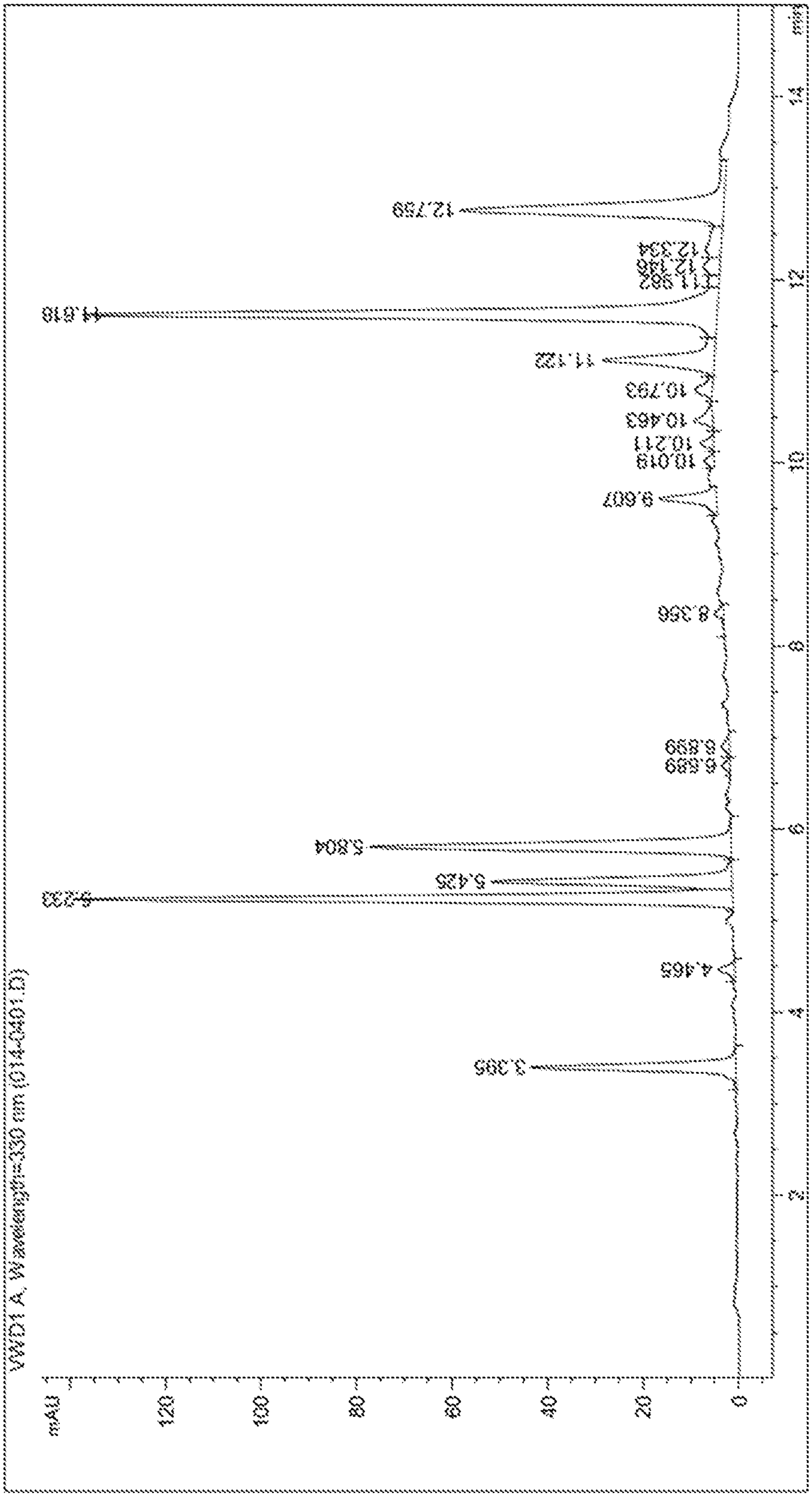
FIG. 2 shows the spectrum of chlorogenic acid in the water extract solution of *Stevia rebaudiana;*

See FIG. 2 for the chlorogenic acid spectrum of the obtained extract solution.

Comparative Example 2

The present Comparative Example provides a method for separating *Stevia rebaudiana* phenols from stevioside, which was operated according method provided by Chinese Patent Publication No. CN105001281B.

Experimental Example 1

The Experimental Example provides a comparison of the contents of partial components of *Stevia rebaudiana* chlorogenic acid in extracts obtained in Example 2 and Comparative Example 1 (traditional water extraction method), and the results were shown in Table 1.

The chlorogenic acid spectrum of the *Stevia rebaudiana* raw material was shown in FIG. 1.

The chlorogenic acid spectrum of the water extract of *Stevia rebaudiana* (Comparative Example 1) was shown in FIG. 2.

Figure 3:
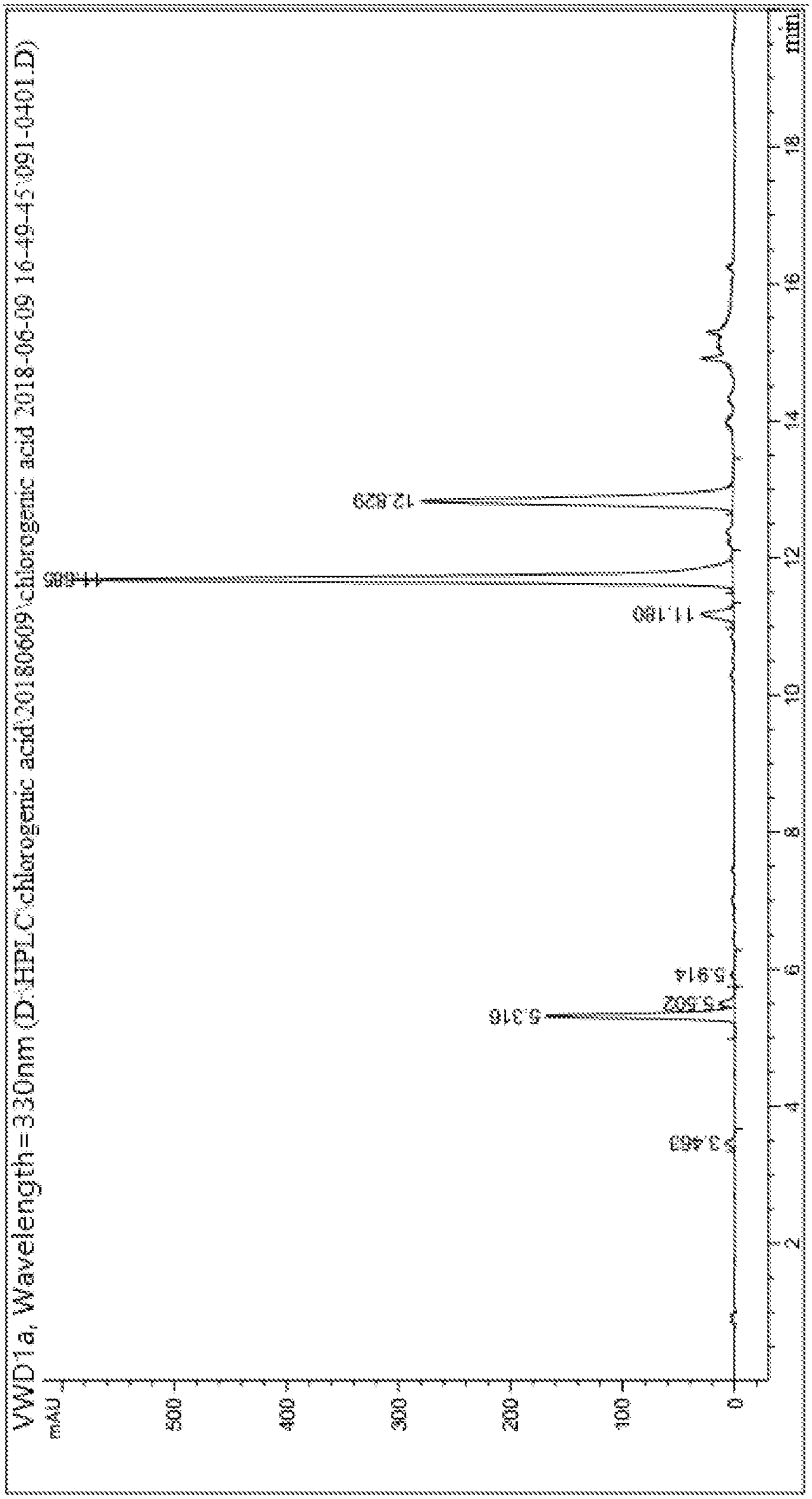
FIG. 3 shows the spectrum of chlorogenic acid in the extract solution obtained in Example 2.

The chlorogenic acid spectrum of the extract obtained in Example 2 was shown in FIG. 3.

TABLE 1

| Proportion of partial components of isochlorogenic acid accounted for in total chlorogenic acid of *Stevia rebaudiana* | Raw material | Water extract solution (prepared in Comparative Example 1) | Extract solution obtained in Example 2 |
|---|---|---|---|
| Mono-caffeoyl substituted chlorogenic acid/% | 20.23 | 38.73 | 13.64 |
| Caffeic acid/% | 0.44 | 14.83 | 0.17 |
| Isochlorogenic acid/% | 79.33 | 45.07 | 85.36 |

Experimental Example 2

The Experimental Example provides a comparison of the technical effects of the separated/prepared stevioside provided in Example 4 to Example 6 and Comparative Examples 1 and 2, the results were shown in Table 2.

TABLE 2

| Detection Index | Comparative Example 1 | Comparative Example 2 | Example 4 | Example 5 | Example 6 |
|---|---|---|---|---|---|
| TSG % | 90 | 91 | 94.3 | 92.9 | 93.6 |
| Light Transmittance (420 nm) | 81 | 83 | 90.8 | 90.3 | 90.6 |
| Specific absorbance (370 nm) | 0.031 | 0.035 | 0.012 | 0.015 | 0.01 |

The total glycoside content in the present application was determined by the GB 8270-2014 method, the light transmittance is a light transmittance at 420 nm under 14% solids concentration detected by UV, and the specific absorbance of stevioside at 370 nm under a concentration of 1% was determined by the GB 8270-1999 method, and the content of total chlorogenic acid and the ratio of each component were determined by the T/CCCMHPIE 1.17-2016 method.

Although a general description, specific embodiments and experiments have been used to describe the present invention in detail above, it is obvious to those skilled in the art that some modifications or improvements can be made on the basis of the present invention. Therefore, all these modifications or improvements made without departing from the spirit of the present invention fall within the protection scope of the present invention.

INDUSTRIAL APPLICABILITY

The present invention provides an industrial method for simultaneously preparing *Stevia rebaudiana* chlorogenic acid and stevioside. The method of the present invention comprises carrying out alcohol extraction on *Stevia rebaudiana* which is used as a raw material, and then adjusting the feed liquid state to allow chlorogenic acid to be in a free molecular state; carrying out extraction-separation with a water-insoluble organic solvent of moderate-polarity; enriching the *Stevia rebaudiana* chlorogenic acid in an organic layer; and enriching the stevioside in a water layer. Compared with a traditional water extraction process, the present invention can prevent chlorogenic acid ingredient in the *Stevia rebaudiana* from being hydrolyzed, such that the contents and effects of effective ingredients in *Stevia rebaudiana* chlorogenic acid products can be guaranteed. Effective separation can be achieved on the premise that the quality and the production efficiency of stevioside products are unaffected, the production efficiency can be greatly improved, and the ratio of isochlorogenic acid to total chlorogenic acid in the resulting products is close to that in the raw material. Water consumption during production can be reduced, and discharge of sewage and flocculation residues can be decreased; and accordingly, the method is a green production process with high benefits, which can greatly promote the progress of the industry, and has good economic value and application prospects.

We claim:

1. A method for preparing chlorogenic acid and stevioside from *Stevia rebaudiana*, the method comprising:

a) extracting *Stevia rebaudiana* powder with an aqueous solution of a short-chain alcohol to obtain a first solution, wherein a solid-to-liquid ratio of the *Stevia rebaudiana* powder to the aqueous solution of the short-chain alcohol is 1:3-7, and the aqueous solution of the short-chain alcohol consists of water and the short-chain alcohol;

b) concentrating the first solution obtained in step a) 5 to 10 times to obtain a second solution;

c) adjusting the second solution obtained in step b) with an acidic reagent to pH 3 to produce a third solution with the chlorogenic acid in a free molecular state, wherein the acidic reagent is selected from one or more of $NaH_2PO_4$, $H_3PO_4$, HCl, $NaHSO_4$, $H_2SO_4$, $H_2CO_3$, $HNO_3$, citric acid, formic acid, oxalic acid, succinic acid and benzoic acid;

d) separating the third solution with an organic solvent to obtain an organic layer and a water layer; and f) collecting the organic layer to obtain a chlorogenic acid extract, and subjecting the water layer to resin adsorption to obtain a stevioside extract;

wherein the acidic reagent is not used in step a).

2. The method of claim 1, wherein in step a), the short-chain alcohol contains 1 to 3 carbon atoms, and a concentration of the aqueous solution of short-chain alcohol is at least 70% by volume.

3. The method of claim 1, wherein step a) is carried out at 40-60° C.

4. The method of claim 1, wherein step b) is carried out at 50-60° C. under a vacuum degree of 0.08 MPa.

5. The method of claim 1, wherein in step d) the organic solvent is water-insoluble and has a polarity of 2.0 to 4.5.

6. The method of claim 1, wherein in step d) the organic solvent is one or more selected from ethyl acetate, dichloromethane, chloroform, diethyl ether and propyl ether.

7. The method of claim 1, wherein in step f) a resin used in the resin adsorption is a low-polarity divinylbenzene type adsorption resin.

8. The method of claim 7, wherein the resin is selected from T28, ADS-750, 69M, DM30 and 201-H.

9. The method of claim 1, wherein in step f) a solid content of the water layer is adjusted to 8% to 12% before the resin adsorption.

10. The method of claim 1, wherein in step f) an adsorption flow rate in the resin adsorption is 0.1 to 0.4 BV/h.

11. The method of claim 1, wherein the chlorogenic acid extract obtained in step f) comprises a dicaffeoylquinic acid and a mono-caffeoylquinic acid.

12. The method of claim 11, wherein the dicaffeoylquinic acid in the chlorogenic acid extract is more than 60% of a total mass of the chlorogenic acid extract.

13. The method of claim 1, wherein in step c), the acidic reagent is formic acid.

* * * * *